United States Patent [19]

Otani

[11] Patent Number: 4,537,182
[45] Date of Patent: Aug. 27, 1985

[54] ENDOSCOPE

[75] Inventor: Yutaka Otani, Tokyo, Japan

[73] Assignee: Olympus Optical Co., Ltd., Tokyo, Japan

[21] Appl. No.: 460,779

[22] Filed: Jan. 25, 1983

[30] Foreign Application Priority Data

Feb. 2, 1982 [JP] Japan ................ 57-15074

[51] Int. Cl.$^3$ .............................................. A61B 1/00
[52] U.S. Cl. ........................................ 128/4; 251/325
[58] Field of Search ............................... 128/4–8; 137/625.68, 605; 251/325

[56] References Cited

U.S. PATENT DOCUMENTS

| 408,145 | 7/1889 | St. John | 137/625.38 |
| 3,958,566 | 5/1976 | Furihata | 128/4 |
| 4,261,343 | 4/1981 | Ouchi et al. | 128/4 |
| 4,270,525 | 6/1981 | Furihata . | |
| 4,361,138 | 11/1982 | Kinoshita | 128/4 |
| 4,412,531 | 11/1983 | Chikashige | 128/4 |

FOREIGN PATENT DOCUMENTS 4810704 6/1967 Japan .

Primary Examiner—Edward M. Coven
Assistant Examiner—Max F. Hindenburg

[57] ABSTRACT

A suction selector mechanism of an endoscope is operated such that a suction channel member may be connected to or disconnected from a suction tube guided to a control section. The selector mechanism has a first connecting port and a second connecting port. The first connecting port is formed in a cylinder and is connected to the suction channel member. The second connecting port is formed in the cylinder and is connected to the suction tube. A piston is slidably inserted in the cylinder and has a circular outer surface portion which is brought into air-tight contact with the cylinder. The piston has an annular small-diameter portion at a position different from that of the outer surface portion. The piston has a channel which allows communication between the space defined by the small-diameter portion and the second connecting port. The first connecting port is closed by the outer surface portion of the piston when the piston is positioned in the non-suction position.

2 Claims, 8 Drawing Figures

FIG. 4
FIG. 5
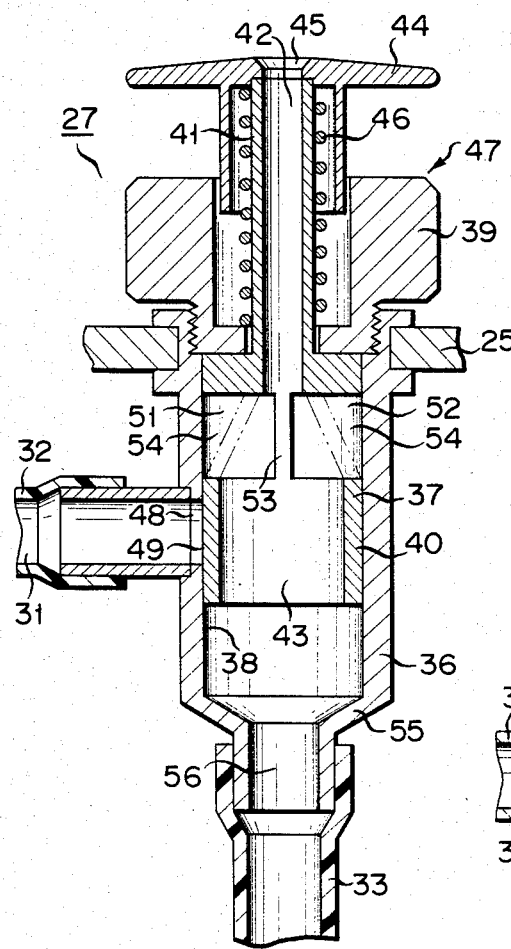
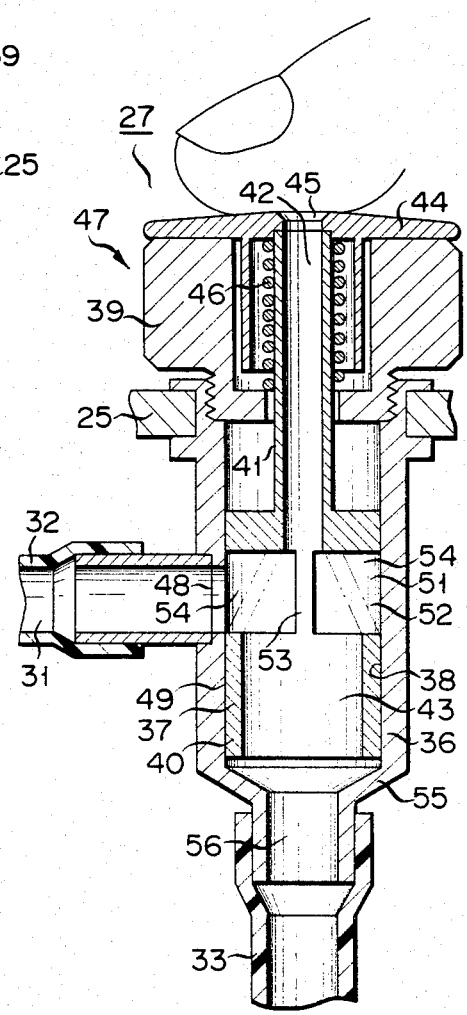

ENDOSCOPE

BACKGROUND OF THE INVENTION

The present invention relates to an endoscope having a suction selector mechanism for opening/closing a suction channel.

A conventional suction selector mechanism of an endoscope is shown in FIGS. 1 and 2, in which a cylindrical piston 2 is slidably fitted in a cylinder 1. An opening 4 communicating with the channel defined by a suction channel member 3 is formed in a side wall of the cylinder 1. A hole portion 6 is formed in the bottom wall of the cylinder 1, and one end of a suction tube 5 is connected thereto. A communicating hole 7 is formed in the piston 2. The piston 2 is urged upward by a coil spring 8. In the non-suction (ready) mode, the piston 2 abuts against an annular stopper 10, as shown in FIG. 1. The opening 4 is not aligned with the communicating hole 7, so that a suction channel 11 is closed. However, as shown in FIG. 2, when the operator closes a leakage hole 12 while pressing the piston 2, that is, when the suction mode is initiated, the opening 4 is aligned with the communicating hole 7, thereby opening the suction channel 11.

In order to guarantee the above selection operation, there must be provided a regulating means which does not allow rotation of the piston 2 but only allows movement of the piston 2 along the axial direction of the cylinder 1. In the conventional mechanism, an elongated groove 14 is formed in the outer surface of the piston 2 along the axial direction thereof, while a pin 15 for preventing rotation of the piston 2 is fixed at a portion of the cylinder 1 such that the pin 15 can be engaged with the elongated groove 14.

In the conventional mechanism having the above configuration, because a pin 15 is required, the number of components increases. Furthermore, the regulating means described above is required, resulting in complex construction and high cost. When the piston 2 is mounted in the cylinder 1, the pin 15 must be engaged with the elongated groove 14. Therefore, the mounting operation, which must be performed every time the mechanism is cleaned and sterilized after use, is very cumbersome and time consuming.

SUMMARY OF THE INVENTION

It is, therefore, an object of the present invention to provide an endoscope which has a suction selector mechanism of a simple construction and which is arranged to allow easy mounting/dismounting of the piston with respect to the cylinder.

In order to achieve the above object of the present invention, there is provided an endoscope which comprises an elongated insertion section having a distal end and a proximal end, said insertion section being adapted to be inserted in a coelic cavity; a control section connected to the proximal end of said insertion section; a suction channel member having first and second ends and being disposed in said insertion section, the first end of said suction channel member being open to the distal end of said insertion section, and the second end of said suction channel member being connected to said control section; a suction tube having first and second ends, the first end of said suction tube being positioned in said control section; and a suction selector mechanism disposed in said control section, which allows connection of the second end of said suction channel member with the first end of said suction tube, and which selectively connects said suction channel member and said suction tube, said suction selector mechanism including a cylinder having an inner surface portion a cross-section of which has a circular shape, a piston having an outer surface disposed inside said cylinder and, as part of the outer surface, a circular outer surface portion being provided such that it is brought into air-tight and slidable contact with the inner surface portion of said cylinder, said piston being capable of adopting a non-pressed position and a pressed position and of moving therebetween, regulating means for regulating movement of said piston between the non-pressed position and the pressed position, urging means for urging said piston into the non-pressed position, an end member which is formed as a unit with said piston and extends toward outside of said control section, a first connecting port which is formed in the inner surface portion of said cylinder and which connects with the second end of said suction channel member, said first connecting port being closed by the circular outer surface portion of said piston when said piston is positioned in the non-pressed position, and being free of the circular outer surface portion of said piston when said piston is positioned in the pressed portion, a small-diameter portion which is formed in an annular shape along the outer surface of said piston and which defines a space with the inner surface portion of said cylinder, said small-diameter portion being positioned opposing said first connecting port when said piston is in the pressed position, a second connecting port disposed in said cylinder and connected to the first end of said suction tube, said second connecting port being positioned outside a range of movement of the circular outer surface portion of said piston, and communicating means, formed in said piston, for communicating the space defined by said small-diameter portion with said second connecting port.

BRIEF DESCRIPTION OF THE DRAWINGS

FIG. 4 is a side sectional view of a suction selector mechanism shown in FIG. 3 in the non-suction mode;

FIG. 5 is a side sectional view of the suction selector mechanism shown in FIG. 4 in the suction mode;

DETAILED DESCRIPTION OF THE PREFERRED EMBODIMENTS

Figure 1:
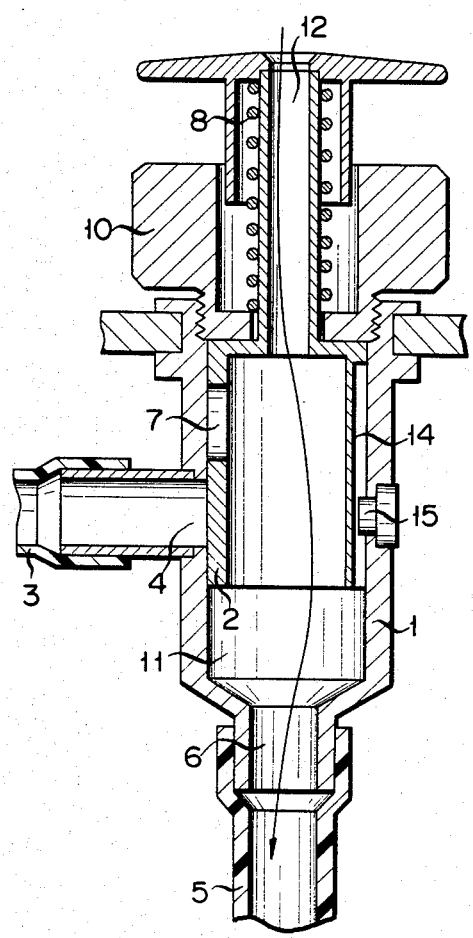
FIG. 1 is a side sectional view of a conventional suction selector mechanism in the non-suction mode.
Figure 2:
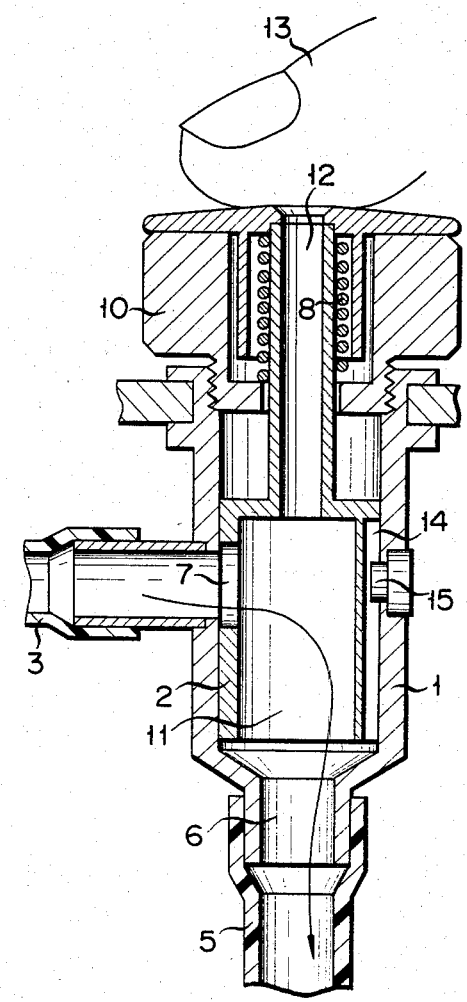
FIG. 2 is a side sectional view of the mechanism shown in FIG. 1 in the suction mode.
Figure 3:
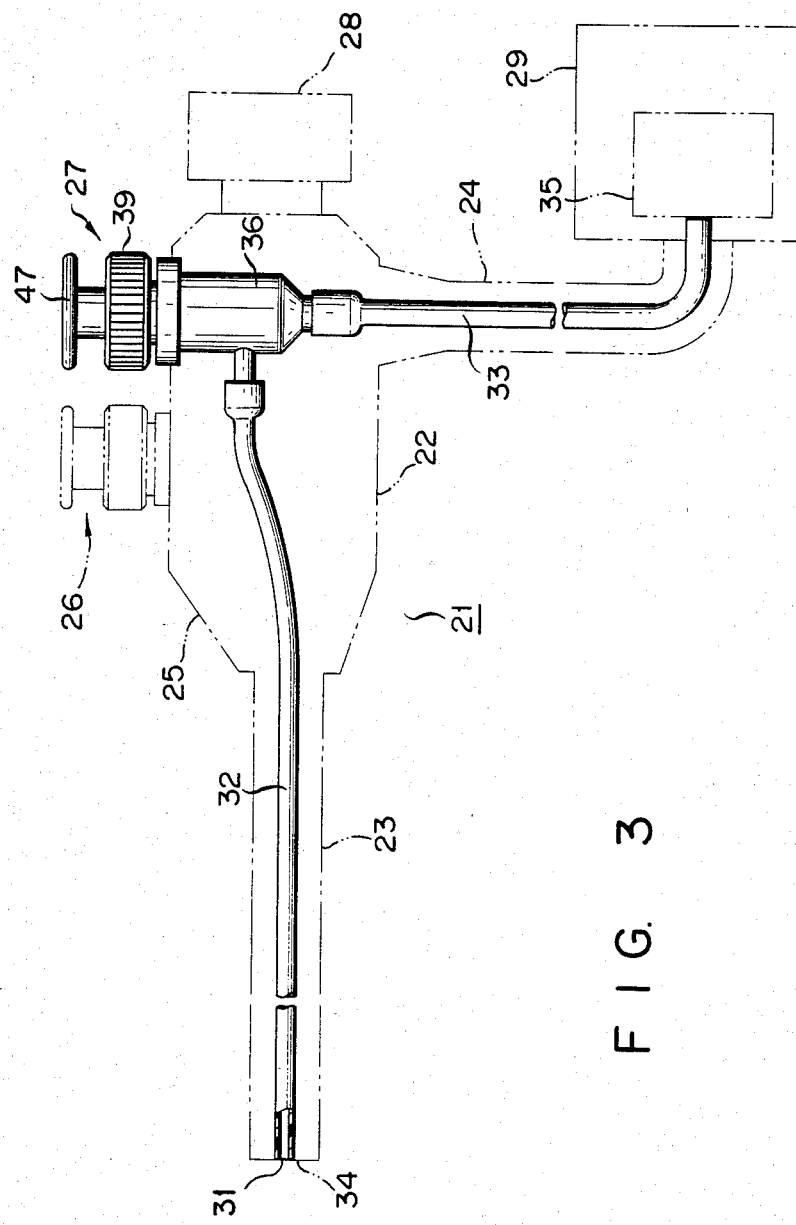
FIG. 3 is a schematic view showing the overall structure of an endoscope according to a first embodiment of the present invention.

As shown in FIG. 3, an endoscope 21 comprises a control section 22, an elongated insertion section 23 which is inserted in a coelic cavity, and a light guide cord 24. The outer wall of the control section 22 is constituted by a cover 25. A selector mechanism 26 for selecting water supply and air supply is disposed next to a suction selector mechanism 27 to be described in detail later on. An eyepiece section 28 is connected to the control section 22. The operator can observe the coelic cavity through the eyepiece section 28. An extended distal end of the light guide cord 24 is connected to a light source device 29. A suction channel 31 extends through the insertion section 23, the control section 22 and the light guide cord 24 of the endoscope 21. The suction channel 31 comprises a suction channel member 32 and a suction tube 33. One end of the suction channel member 32 is open at a distal end 34 of the insertion section 23, and the other end thereof reaches the control section 22. One end of the suction tube 33 is disposed at the control section 22, and the other end thereof is guided to the light source device 29 through the light guide cord 24. The other end of the suction tube 33 is connected to a suction source 35 disposed in the light source device 29. A pump (not shown) or the like can be used as the suction source 35. The suction selector mechanism 27 is disposed between the suction channel member 32 and the suction tube 33.

Figure 6:
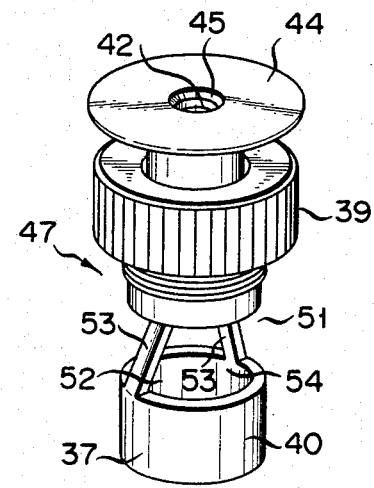
FIG. 6 is a perspective view of a control unit of the mechanism shown in FIG. 4.

The suction selector mechanism 27 has a structure as shown in FIGS. 4 to 6. The suction selector mechanism 27 has a cylinder 36 and a piston 37. The cylinder 36 comprises a cylindrical metal member with a bottom, such that one end thereof is closed and the other end is open. An inner surface portion 38 of the cylinder 36 has a circular cross-section of a constant diameter over its entire length. The edge of the open end of the cylinder 36 is fixed to the cover 25 of the control section 22. An annular stopper 39 is detachably mounted at the open end of the cylinder 36 by screw-mounting means.

The piston 37 comprises a fitting portion 40 which is slidably fitted along the inner surface portion 38 of the cylinder 36. An end portion 41 (of the control section 22) which outwardly extends through the annular stopper 39 is integrally formed with the fitting portion 40. The diameter of the end portion 41 is smaller than that of the fitting portion 40. The fitting portion 40 and the end portion 41 as a whole have a hollow cylindrical shape. A leakage hole 42 is formed in a hollow part of the end portion 41 and can communicate with the outside of the control section 22. The leakage hole 42 communicates with a hollow portion 43 formed in the fitting portion 40. The diameter of the hollow portion 43 of the fitting portion 40 is greater than that of the leakage hole 42. In other words, the hollow portion 43 must be formed to be as large as possible so as to decrease flow resistance in the channel 31 and to increase the flow rate.

A control button 44 is disposed at the outer end of the end portion 41. An opening 45 is formed in the control button 44 to communicate with the leakage hole 42.

A coil spring 46 is wound around the end portion 41. The coil spring 46 extends between the annular stopper 39 and the control button 44 and urges the piston 37 toward the outside of the control section 22. Therefore, the end face of the fitting portion 40 abuts against the annular stopper 39 so as to keep the piston in the non-suction position, as shown in FIG. 4. However, as shown in FIG. 5, when the operator presses the piston 37, the control button 44 abuts against the annular stopper 39, so that the piston 37 is kept in a position corresponding to the suction mode. In brief, the annular stopper 39 abuts against either the end face of the control button 44 or the fitting portion 40 (piston 37) so as to determine the suction or non-suction mode, respectively. The annular stopper 39 thus serves as a regulating means for regulating movement of the piston 37. The coil spring 46 serves as an urging means for urging the piston 36 into a position corresponding to the non-suction mode. The piston 37, the annular stopper 39, the control button 44, and the coil spring 46 constitute a control unit 47 which is detachable from the cylinder 36 as shown in FIG. 6.

A first connecting port 48 is open to the inner surface portion 38 of the cylinder 36 and is connected to the other end of the suction channel member 32. The first connecting port 48 may be closed in the non-suction mode by an outer surface portion 49 of the piston 37. The outer surface portion 49 of the piston 37 is of a cylindrical shape so as to fittingly engage with the inner surface portion 38 of the cylinder 36. The outer surface portion 49 is brought into air-tight contact with the inner surface portion 38 of the cylinder 36 and is slidable therealong. A small-diameter portion 51 is formed at a peripheral part of the fitting portion 40 of the piston 37, which peripheral part of the fitting portion 40 is closer to the annular stopper 39 than is the outer surface portion 49. The small-diameter portion 51 has an annular shape along the perimeter of the edge of the piston 37 so as to define a space 52 between the small-diameter portion 51 and the inner surface portion 38 of the cylinder 36. The space 52 defined by the small-diameter portion 51 communicates with the hollow portion 43 of the piston 37. When the operator presses the control button 44, the space 52 defined by the small-diameter portion 51 communicates with the first connecting port 48. The small diameter portion 51 has a wall which comprises a pair of columns 53 formed by notching the fitting portion 40, thus forming a pair of holes 54. The space 52 and the hollow portion 43 communicate with each other through the holes 54. The small-diameter portion 51 is tapered toward the annular stopper 39.

A second connecting port 56 is formed in a bottom wall 55 of the cylinder 36 and can be connected to one end of the suction tube 33. The second connecting port 56 communicates with the space 52 defined by the small-diameter portion 51 through the bottom space of the cylinder 36, the hollow portion 43 of the piston 37, and the holes 54 of the small-diameter portion 51. The hollow portion 43 of the piston 37 and the holes 54 constitute a channel means for allowing communication between the space 52 and the second connecting port 56. It is noted that the second connecting port 56 constantly communicates with the hollow portion 43.

The operation of the suction selector mechanism 27 will be described in detail.

In the non-suction mode, the suction selector mechanism 27 is positioned as shown in FIG. 4. In this condition, the first connecting port 48 is air-tightly closed by the outer surface portion 49 of the piston 37. The second connecting port 56 communicates with the outside of the control section 22 through the hollow portion 43 of the piston 37. When the suction source 35 is operated to perform suction through the suction tube 33, the suction source 35 only draws air from the control section 22 through the hollow portion 43. As a result, no suction effect is produced on the side of the suction channel 32.

In the suction mode, the operator closes the opening 45 of the control button 44 with a finger and presses the control button 44, as shown in FIG. 5. The piston 37 is moved downward and is stopped when the control button 44 abuts against the annular stopper 39, as shown in FIG. 5. Since the space 52 defined by the small-diameter portion 51 then communicates with the first connecting port 48, the first connecting port 48 communicates with the second connecting port 56 through the space 52, the holes 54 and the hollow portion 43. Furthermore, since the opening 45 of the control button 44 is closed by the operator's finger, external air may not be drawn therethrough. Therefore, the suction force is only applied to the side of the suction channel member 32. A fluid is drawn from the coelic cavity through the suction channel 32. In this condition, the total space of the hollow portion 43 and the holes 54 is sufficiently greater than that of the first and second connecting ports 48 and 56 to decrease resistance to the fluid when the fluid passes through the hollow portion 43 and the holes 54.

When the operator wishes to clean and sterilize the endoscope 21, he can remove the annular stopper 39 from the cylinder, thus completely removing the control unit 47 of the selector mechanism 27 from the cylinder 36. When sterilization is finished, the control unit 47 can be readily mounted in the cylinder 36. In this mounting operation, the operator need not consider the rotational direction of the piston 37, but simply inserts the control unit 47 in the cylinder 36. Since the annular small-diameter portion 51 is formed in the fitting portion 40 of the piston 37, the space 52 defined by the small-diameter portion 51 constantly communicates with the first connecting port 48. In other words, directivity need not be considered when the piston 37 is mounted in the cylinder 36.

Figure 7:
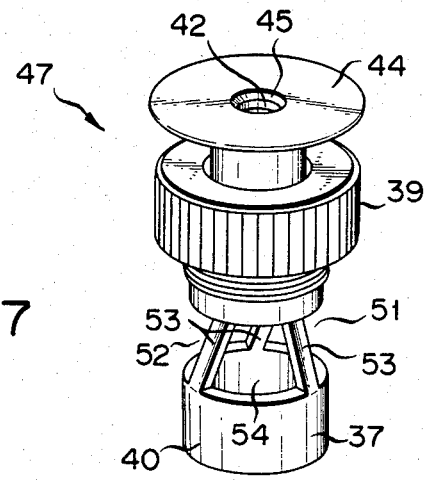
FIG. 7 is a perspective view of a control unit of an endoscope according to a second embodiment of the present invention.

FIG. 7 is a control unit 47 of an endoscope according to a second embodiment of the present invention. In this embodiment, a small-diameter portion 51 has three columns 53 and three corresponding holes 54.

Figure 8:
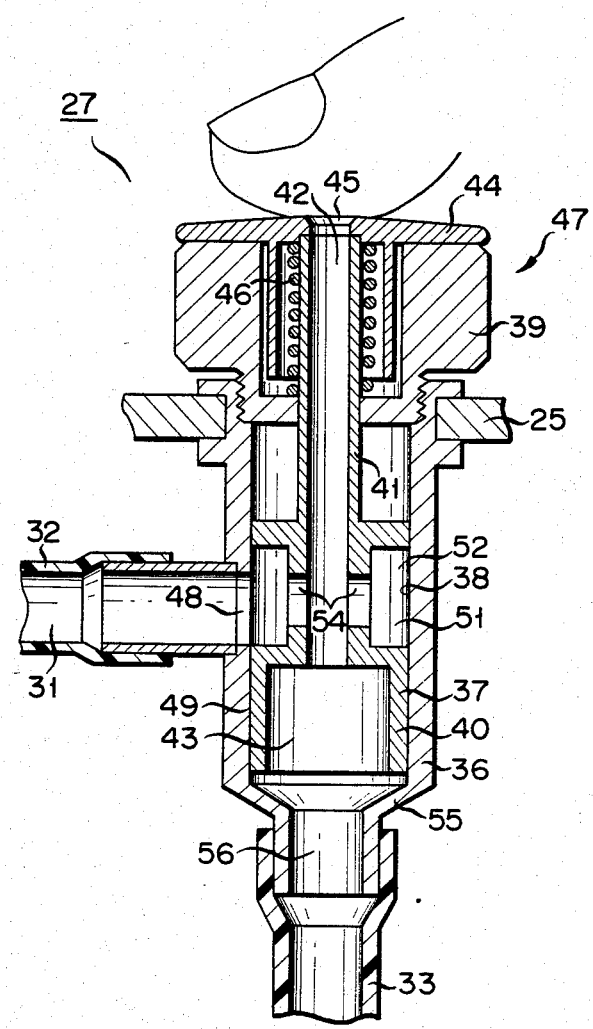
FIG. 8 is a side sectional view of a suction selector mechanism of an endoscope according to a third embodiment of the present invention, in the suction mode.

FIG. 8 shows a suction selector mechanism of an endoscope according to a third embodiment of the present invention. A small-diameter portion 51 is of a cylindrical shape; it is not tapered. A plurality of holes 54 are formed in the wall of the small-diameter portion 51.

According to the present invention, the piston need not be aligned with a given surface portion of the cylinder, and can be simply fitted in the cylinder. Furthermore, since only the small-diameter portion is formed in the piston, a means is not required to prohibit rotation of the piston, thus simplifying the construction of the mechanism as a whole. Therefore, the number of component parts is decreased, thus decreasing the number of assembly steps.

What is claimed is:

1. An endoscope comprising:
   (i) an elongated insertion section having a distal end and a proximal end, said insertion section being adapted to be inserted in a coelic cavity;
   (ii) a control section connected to the proximal end of said insertion section;
   (iii) a suction channel member having first and second ends disposed in said insertion section, the first end of said suction channel member being open to the distal end of said insertion section, and the second end of said suction channel member being connected to said control section;
   (iv) a suction tube having first and second ends, the first end of said suction tube being positioned in said control section; and
   (v) a suction selector mechanism disposed in said control section, which allows connection of the second end of said suction channel member with the first end of said suction tube, and which selectively connects said suction channel member and said suction tube, said suction selector mechanism including:
      (a) a cylinder having an inner surface portion a cross-section of which has a circular shape,
      (b) a piston having an outer surface disposed inside said cylinder and, as part of the outer surface, a circular outer surface portion being provided such that it is brought into air-tight and slidable contact with the inner surface portion of said cylinder, said piston being capable of adopting a non-pressed position and a pressed position and of moving therebetween,
      (c) regulating means for regulating movement of said piston between the non-pressed position and the pressed position,
      (d) urging means for urging said piston into the non-pressed position,
      (e) an end portion which is formed as a unit with said piston and extends therefrom toward said regulating means,
      (f) a first connecting port which is formed in the inner surface portion of said cylinder and which connects with the second end of said suction channel member, said first connecting port being closed by the circular outer surface portion of said piston when said piston is positioned in the non-pressed position, and being freed of the circular outer surface portion of said piston when said piston is positioned in the pressed portion,
      (g) a small-diameter portion which is formed along the outer surface of said piston and which defines a space with the inner surface portion of said cylinder, said small-diameter portion being positioned opposing said first connecting port when said piston is in the pressed position,
      (h) a second connecting port disposed in said cylinder and connected to the first end of said suction tube, said second connecting port being positioned outside a range of movement of the circular outer surface portion of said piston,
      (i) communicating means, formed in said piston, for communicating the space defined by said small-diameter portion with said second connecting port, said end portion of said piston having a leakage hole of a certain diameter communcating with the outside of said control section, said piston having said communicating means and a hollow chamber which communicates with said leakage hole, said hollow chamber having a diameter greater than the diameter of said leakage hole, the outer surface of said small-diameter portion being tapered from said leakage hole towards said hollow chamber and having a hole continuously open to said hollow chamber.

2. An endoscope according to claim 1, wherein said small-diameter portion has a wall which comprises a plurality of columns, said plurality of columns having spaces therebetween which communicate with said hollow chamber.

* * * * *